US00PP24242P2

(12) United States Plant Patent
Isobe

(10) Patent No.: US PP24,242 P2
(45) Date of Patent: Feb. 11, 2014

(54) ***PETUNIA* PLANT NAMED 'SUNSURF DENIUSA'**

(50) Latin Name: *Petunia×hybrida*
Varietal Denomination: Sunsurf Deniusa

(75) Inventor: Yasuko Isobe, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 76 days.

(21) Appl. No.: 13/506,173

(22) Filed: Mar. 31, 2012

(51) Int. Cl.
*A01H 5/00* (2006.01)

(52) U.S. Cl.
USPC ..... Plt./356.1

(58) Field of Classification Search
USPC ..... Plt./356.1
See application file for complete search history.

*Primary Examiner* — Annette Para
(74) *Attorney, Agent, or Firm* — C. A. Whealy

(57) ABSTRACT

A new and distinct cultivar of *Petunia* plant named 'Sunsurf Deniusa', characterized by its compact and mounding plant habit; vigorous growth habit; freely branching habit; early and freely flowering habit; long flowering period; small violet-colored flowers with white-colored throats; and good garden performance.

1 Drawing Sheet

Botanical designation: *Petunia×hybrida*.
Cultivar denomination: 'SUNSURF DENIUSA'.

BACKGROUND OF THE INVENTION

The present invention relates to a new and distinct cultivar of *Petunia* plant, botanically known as *Petunia×hybrida* and hereinafter referred to by the name 'Sunsurf Deniusa'.

The new *Petunia* plant is a product of a planned breeding program conducted by the Inventor in Higashiomi, Shiga, Japan. The objective of the breeding program is to create new compact freely branching and freely flowering *Petunia* plants with mounding habit and attractive flower coloration.

The new *Petunia* plant originated from a cross-pollination made by the Inventor in July, 2008 in Higashiomi, Shiga, Japan of a proprietary selection of *Petunia×hybrida* identified as code name BDV01, not patented, as the female, or seed, parent with a proprietary selection of *Petunia×hybrida* identified as code name Px314-2, not patented, as the male, or pollen, parent. The new *Petunia* plant was discovered and selected by the Inventor as a single flowering plant within the progeny of the stated cross-pollination in a controlled environment in Higashiomi, Shiga, Japan in June, 2009.

Asexual reproduction of the new *Petunia* plant by terminal cuttings in a controlled environment in Higashiomi, Shiga, Japan since June, 2009 has shown that the unique features of this new *Petunia* plant are stable and reproduced true to type in successive generations.

SUMMARY OF THE INVENTION

Plants of the new *Petunia* have not been observed under all possible environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunsurf Deniusa'. These characteristics in combination distinguish 'Sunsurf Deniusa' as a new and distinct *Petunia* plant:

1. Compact and mounding plant habit.
2. Vigorous growth habit.
3. Freely branching habit.
4. Early and freely flowering habit.
5. Long flowering period.
6. Small violet-colored flowers with white-colored throats.
7. Good garden performance.

Plants of the new *Petunia* can be compared to plants of the female parent selection. Plants of the new *Petunia* differ primarily from plants of the female parent selection in flower size as plants of the new *Petunia* have smaller flowers than plants of the female parent selection.

Plants of the new *Petunia* can be compared to plants of the male parent selection. Plants of the new *Petunia* differ primarily from plants of the male parent selection in branching habit as plants of the new *Petunia* are more freely branching than plants of the male parent selection. In addition, plants of the new *Petunia* have darker violet-colored flowers than plants of the male parent selection.

Plants of the new *Petunia* can also be compared to plants of the *Petunia* 'Sunsurfcoparu', disclosed in U.S. Plant Pat. No. 18,141. In side-by-side comparisons conducted in Higashiomi, Shiga, Japan, plants of the new *Petunia* and 'Sunsurfcoparu' differed primarily in the following characteristics:

1. Plants of the new *Petunia* had smaller leaves than plants of 'Sunsurfcoparu'.
2. Plants of the new *Petunia* had smaller flowers than plants of 'Sunsurfcoparu'.
3. Plants of the new *Petunia* and 'Sunsurfcoparu' differed in flower color as plants of 'Sunsurfcoparu' had red purple-colored flowers.
4. Plants of the new *Petunia* had shorter peduncles than plants of 'Sunsurfcoparu'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunsurf Deniusa' grown in a container.

The photograph at the bottom of the sheet is a close-up view of a typical flowering plant of 'Sunsurf Deniusa'.

DETAILED BOTANICAL DESCRIPTION

The aforementioned photographs and following observations, measurements and values describe plants grown during the autumn in 15-cm containers in an outdoor nursery in Higashiomi, Shiga, Japan and under cultural practices typical of commercial production. During the production of the plants, day temperatures averaged 23° C. and night temperatures averaged 13° C. Plants were four months old when the photographs and description were taken. In the following description, color references are made to The Royal Horticultural Society Colour Chart, 2001 Edition, except where general terms of ordinary dictionary significance are used.

Botanical classification: *Petunia×hybrida* 'Sunsurf Deniusa'.

Parentage:

*Female, or seed, parent*.—Proprietary selection of *Petunia×hybrida* identified as code name BVD01, not patented.

*Male, or pollen, parent*.—Proprietary selection of *Petunia×hybrida* identified as code name Px314-2, not patented.

Propagation:

*Type*.—By terminal cuttings.

*Time to initiate roots*.—About one week at temperatures of 15° C. to 20° C.

*Time to produce a rooted young plant*.—About three weeks at temperatures of 15° C. to 20° C.

*Root description*.—Fibrous; white in color.

*Rooting habit*.—Freely branching.

Plant description:

*Plant and growth habit*.—Compact and mounding plant habit; freely branching habit with numerous lateral branches developing per plant; pinching enhances lateral branch development; vigorous growth habit.

*Plant height*.—About 15.2 cm.

*Plant diameter*.—About 38.9 cm.

Lateral branch description:

*Length*.—About 17.8 cm.

*Diameter*.—About 1.5 mm.

*Internode length*.—About 1.7 cm.

*Strength*.—Strong, flexible.

*Aspect*.—Upright to outwardly.

*Texture*.—Pubescent.

*Color*.—Close to 144B.

Foliage description:

*Arrangement*.—Alternate, simple.

*Length*.—About 3.9 cm.

*Width*.—About 1.4 cm.

*Shape*.—Elliptic.

*Apex*.—Narrowly acute.

*Base*.—Attenuate.

*Margin*.—Entire.

*Texture, upper and lower surfaces*.—Pubescent.

*Venation pattern*.—Pinnate; reticulate.

*Color*.—Developing and fully expanded leaves, upper surface: Close to 143A; venation, close to 144B. Developing and fully expanded leaves, lower surface: Close to 138B; venation, close to 144D.

*Petioles*.—Length: About 6 mm. Diameter: About 0.8 mm. Texture, upper and lower surfaces: Pubescent. Color, upper and lower surfaces: Close to 144B.

Flower description:

*Flower arrangement and habit*.—Single salverform flowers arising from upper leaf axils; freely flowering habit with usually about 22 flowers developing per plant; flowers face upright to outwardly.

*Fragrance*.—None detected.

*Natural flowering season*.—Early flowering habit, plants of the new *Petunia* initiate and develop flowers about two weeks after planting; long flowering period; flowering commences naturally during the spring and plants flower continuously throughout the summer until late autumn in Japan.

*Flower longevity*.—Individual flowers last about seven to ten days on the plant; flowers not persistent.

*Flower diameter*.—About 3.7 cm.

*Flower length (depth)*.—About 3.5 cm.

*Throat diameter*.—About 1.1 cm.

*Tube diameter, base*.—About 2.8 mm.

*Tube length*.—About 2.5 cm.

*Flower buds*.—Shape: Cylindrical. Length: About 3.1 cm. Diameter: About 6.9 mm. Color: Close to NN155C; towards the apex, close to 86D; venation, close to 143B.

*Corolla*.—Arrangement: Five petals fused at the base and opening into a flared trumpet. Petal length from throat: About 1.6 cm. Petal width: About 1.8 cm. Petal shape: Spatulate. Petal apex: Cuspidate. Petal margin: Entire, slightly undulate. Petal texture, upper and lower surfaces: Smooth, glabrous. Throat texture: Smooth, glabrous. Tube texture: Pubescent. Color: Petal, when opening and fully opened, upper surface: Close to N87A. Petal, when opening and fully opened, lower surface: Close to 84A. Throat: Close to NN155C; towards the petal lobes, close to N87B. Tube: Close to NN155C.

*Calyx*.—Arrangement: One star-shaped calyx tube with five sepals fused at the base per flower. Sepal length: About 1.8 cm. Sepal width: About 3.1 mm. Sepal shape: Narrowly elliptic. Sepal apex: Obtuse. Sepal margin: Entire. Sepal texture, upper and lower surfaces: Pubescent. Color: Developing sepals, upper surface: Close to 143A. Developing sepals, lower surface: Close to 143C. Fully developed sepals, upper surface: Close to 143A. Fully developed sepals, lower surface: Close to 143B.

*Peduncles*.—Length: About 2.4 cm. Diameter: About 0.8 mm. Strength: Strong. Texture: Pubescent. Color: Close to 144B.

*Reproductive organs*.—Stamens: Quantity per flower: Five. Stamen length: About 1.3 cm to 1.7 cm. Anther shape: Ellipsoidal. Anther size: About 2 mm by 1.6 mm. Anther color: Close to 85B. Pollen amount: Scarce. Pollen color: Close to 85C. Pistils: Quantity per flower: One. Pistil length: About 1.5 cm. Style color: Close to 144B. Stigma shape: Transversely ellipsoidal. Stigma color: Close to 144A. Ovary color: Close to 144A. Seeds and fruits: Seed and fruit development have not been observed on plants of the new *Petunia*.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants.

It is claimed:

1. A new and distinct *Petunia* plant named 'Sunsurf Deniusa' as illustrated and described.

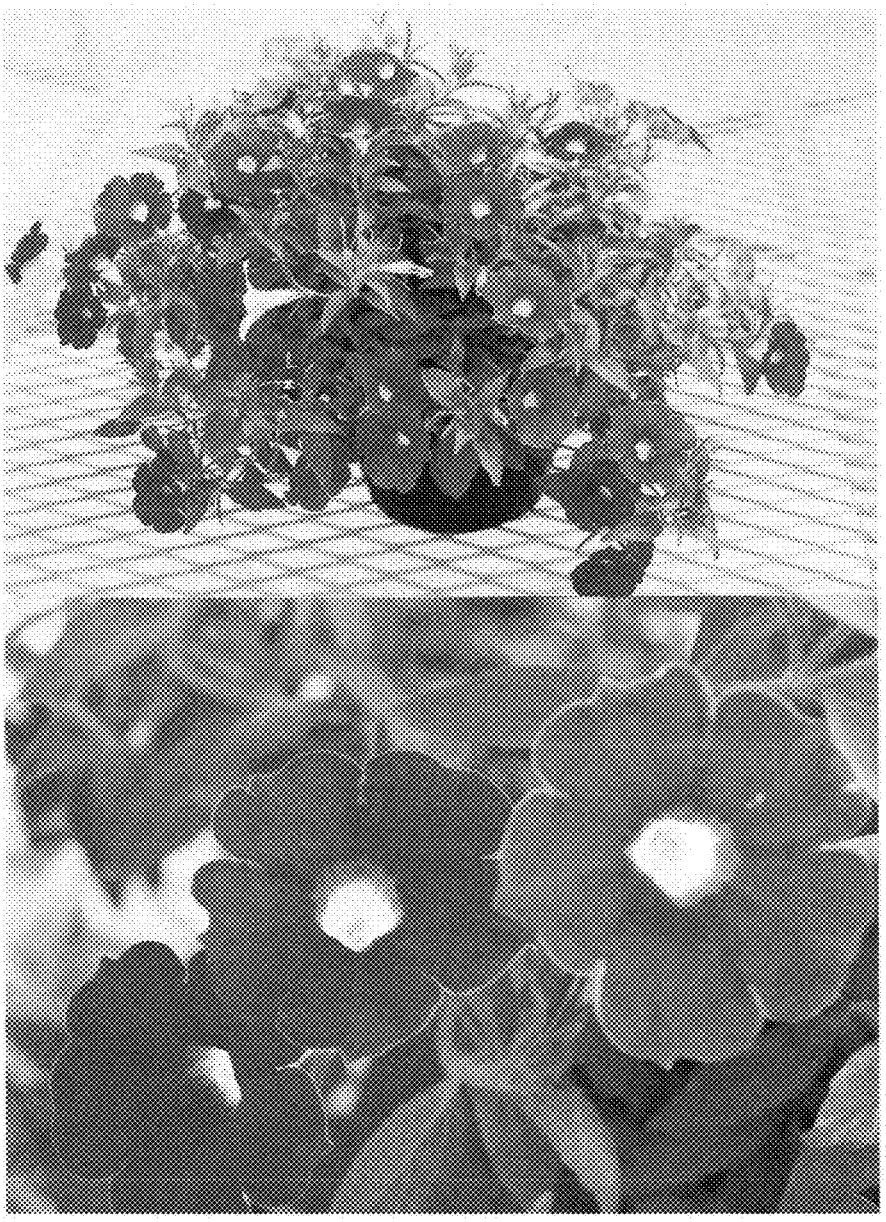

* * * * *